United States Patent [19]

Brandley et al.

[11] Patent Number: 5,087,337
[45] Date of Patent: *Feb. 11, 1992

[54] FLUORESCENT TAG FOR SUGAR ELECTROPHORESIS

[75] Inventors: Brian K. Brandley, Alameda; Michael Tiemeyer, Oakland; Robert J. Stack, Alameda, all of Calif.

[73] Assignee: Glycomed, Inc., Alameda, Calif.

[*] Notice: The portion of the term of this patent subsequent to Dec. 4, 2007 has been disclaimed.

[21] Appl. No.: 589,441

[22] Filed: Sep. 27, 1990

Related U.S. Application Data

[63] Continuation-in-part of Ser. No. 483,043, Feb. 16, 1990, Pat. No. 5,035,786.

[51] Int. Cl.$^5$ .............................. G01N 27/26
[52] U.S. Cl. ..................... 204/182.1; 204/182.8; 204/299 R; 536/127
[58] Field of Search ............... 204/180.1, 182.1, 182.8, 204/299 R; 536/127

[56] References Cited

U.S. PATENT DOCUMENTS

| | | | |
|---|---|---|---|
| 4,109,075 | 8/1978 | Deaton | 536/1 |
| 4,305,799 | 12/1981 | Schwarz et al. | 204/299 R |
| 4,666,581 | 5/1987 | Itoh et al. | 204/299 R |

*Primary Examiner*—John Niebling
*Assistant Examiner*—David G. Ryser
*Attorney, Agent, or Firm*—Morrison & Foerster

[57] ABSTRACT

A method of separating mixtures of saccharides into distinct detectable groups is disclosed. In accordance with the method a tri-functional conjugate must first be provided. The tri-functional conjugate is obtained by reacting a mixture of saccharides with moieties (a) capable of providing a charge upon ionization; (b) capable of fluorescing under ultraviolet light; and (c) having a light-activatable azido group thereon. The different functional moieties may all be present on the same moiety and connected directly to the saccharide or may be connected to each other wherein only one of the moieties is connected directly to the saccharide. The tri-functional conjugates are subjected to electrophoretic separation to obtain separate groups of conjugates in the gel. The groups of conjugates are transferred from the gel to the surface of a membrane which is exposed to light for a sufficient time and light frequency to activate the azido-group. The light-activated azido-groups attached to the surface of the membrane. The tri-functional conjugates can then be contacted with labeled probes such as radiolabeled proteins to determine the affinity of the probes to particular saccharides.

27 Claims, No Drawings

FLUORESCENT TAG FOR SUGAR ELECTROPHORESIS

CROSS-REFERENCE

This application is a continuation-in-part of our pending, U.S. application Ser. No. 483,043 filed Feb. 16, 1990 now U.S. Pat. No. 5,035,786, which application is incorporated herein by reference and to which application we claim priority under 35 U.S.C. §120.

Further, this application is related in part to two other co-pending U.S. applications filed concurrently with the present application on Sept. 27, 1990. One related application is entitled "Two-Dimensional Electrophoretic Separation of Carbohydrates" invented by Brian K. Brandley and Robert J. Stach; the other application is entitled "Electro-Blotting of Electrophoretically Resolved Fluorescent-Labeled Saccharides and Detection of Active Structures With Protein Probes" invented by Brian K. Brandley, Paul G. James, Michael Tiemeyer and Robert J. Stach, all of whom are inventors working in the same research organization as the present inventors with an obligation to assign the invention to the same entity. The above-referenced applications are each incorporated herein by reference in their entireties.

FIELD OF THE INVENTION

This inventions relates generally to the field of electrophoretic separation and electro-blotting techniques. More specifically, the invention relates to separating mixtures of saccharides with electrophoresis and electro-blotting the separated saccharides while using a fluorescent tag which binds to and charges the saccharides and a light-activatable azido-group.

BACKGROUND OF THE INVENTION

Electrophoresis is a well known technique for the separation of a charged species by utilizing their differences in rate of migration under the influence of an electrical field. The procedure has proved invaluable for the resolution and isolation of complex biological substances such as enzymes, serums, carbohydrates, proteins, DNA and RNA. Most analytical electrophoresis methods are based on zone-electrophoresis in which a thin zone of a sample material is applied to the electrophoretic medium. The electrophoretic migration of the sample components results in the formation of fractional zones. These zones can be examined and studied by applications of standard electrophoretic practice such as fixing, staining and washing to remove buffers. Desirably, the electrophoretic media is a thin gel film coated on a suitable support, commonly glass or plastic. Such an arrangement permits the electrophoretic separation to be achieved in a minimum of time with a maximum degree of resolution.

Various hydrophilic colloids, for example, starch, agarose and cellulose derivatives have been used in forming electrophoretic gel films, but polyacrylamide is preferred. One reason for preferring polyacrylamide is that gels can be prepared from it having a wide range of pore size. This is accomplished primarily by varying the ratio of acrylamide polymer to the N, N', methylenebisacrylamide cross-linking reagent.

The resulting polyacrylamide gels provide high resolution electrophoretic separation of important biopolymers, for example, proteins and nucleic acids. In addition, the absence of ionized groups in polyacrylamide gels render such gels suitable as an anticonvection medium for isoelectric focusing.

Once the electrophoretic techniques have been applied in order to separate the materials in the gel, it is necessary to transfer the separated materials from the gel to a support where they can be tested. A number of procedures are available for transferring the electrophoretically resolved materials from the gel. One such procedure involves electro-blotting. This type of transfer procedure involves transferring the resolved bands within the gel to a support matrix such as a nitrocellulose sheet. The transfer is carried out by the application of an electric field and therefore is distinguishable from a more conventional alternative which involves the capillary transfer of such materials usually used in techniques such as southern and northern blotting.

SUMMARY OF THE INVENTION

The present invention provides a method for separating mixtures of saccharides into distinct detectable groups. The method is carried out by reacting a mixture of saccharides with a charge generating moiety which is also capable of fluorescing and includes an azido group. This charge generating moiety is preferably a modified form of 1-amino-4-naphthalene sulfonic acid (hereinafter ANSA). The reaction is carried out in order to form saccharide conjugates which are charged, include an azido group and can fluoresce under U.V. light.

An important aspect of the invention involves the modification of the charge generating fluorescent molecules by the addition of a light-sensitive azido-group. The light-sensitive azido group is protected from light until its activation is desired. Upon activation of the azido group the conjugate reacts with the substrate and becomes bonded thereto.

After the conjugates are formed, they are subjected to gel electrophoresis for a sufficient period of time to form separate groups of conjugates in bands in the electrophoresis gel. The bands of conjugates are transferred from the gel to the surface of a membrane by electro-blotting procedures. Thereafter, the conjugates on the surface of the substrate are subjected to light for a sufficient period of time and a sufficient frequency in order to activate the light-sensitive azido-group which when activated substantially increases the affinity of the group to the membrane surface.

The securely bound conjugates can be visually detected because the group capable of fluorescing, such as napthalene, will fluoresce when exposed to U.V. light. The fluorescent conjugates can then be contacted with labeled probes, such as labeled protein probes, in order to determine the affinity of the protein to particular groups of saccharides.

A primary object of the invention is to provide a method of separating mixtures of saccharides into distinct detectable groups which can then be readily assayed for their affinity to particular molecules, such as proteins attached to detectable probes.

An advantage of the present invention is that the separation procedure provides visually detectable distinct groups of saccharides on a substrate surface.

A feature of the present invention is that the separated groups of saccharides provided on a substrate surface by electro-blotting are caused to have greater affinity for the substrate surface by a light activatable azido-group attached to the charge generating group capable of fluorescing.

The important features of the invention which contributed to the overall objects and advantages of the invention are the inclusion of the charge-generating group which provides for the sensitive separation procedures using electrophoresis methodology, the inclusion of a group capable of fluorescing which provides for the visibility of small bands of separated material when viewed under ultraviolet light and inclusion of the light-activatable azido group which allows for the conjugates to be easily moved until they are exposed to light at which point they bind tightly to a substrate and allow the conjugates to be assayed for their affinity to other compounds.

These and other objects, advantages and features of the present invention will become apparent to those persons skilled in the art upon reading the details of the structure, synthesis and usage as more fully set forth below, reference being made to the accompanying general structural formula forming a part hereof.

DETAILED DESCRIPTION OF PREFERRED EMBODIMENTS

Before the present invention for separating, labeling and testing oligosaccharides is described, it is to be understood that this invention is not limited to the particular oligosaccharides, labels, proteins or process steps described as such compounds and steps may, of course, vary. It is also to be understood that the terminology used herein is for purposes of describing particular embodiments only and is not intended to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to "a saccharide" includes mixtures of saccharides, reference to "an azido-group" includes reference to mixtures of such groups, and reference to "the electophoretic processing step" includes a variety of similar steps of type described herein.

In order to carry out the invention the carbohydrates or saccharides which are to be subjected to electrophoretic separation techniques must first be correctly prepared. This is done by attaching to the saccharides three different functional moieties which may be present on a single moiety or may be attached separately. Accordingly, these moieties can be attached in a single reaction (when they are all present on a single moiety) by two reactions (when two functional groups are present on a single moiety and one on another) or by three separate reactions whereby three separate functional moieties are individually attached to the carbohydrate. Ultimately, it is important that the carbohydrates to be separated are reacted with a moiety which (1) provides a charge; (2) is capable of fluorescing; and (3) includes a light-activatable azido group. The moiety capable of generating a charge is necessary in order to utilize electrophoretic separation techniques which rely on the application of a charged field to separate. The group capable of fluorescing is used in order to make it possible to visually identify separated bands of material when the materials are viewed under ultraviolet light. Advantages of the use of these fluorescent groups are described further below. The presence of the light-activated azido group makes it possible to easily move the materials from one substrate or material to another prior to the activation of a group and thereafter secure the material to a substrate by exposing the material to the light and activating the azido group which then binds to the substrate. When the material is bound to the substrate it can be exposed to other materials which are to be assayed for their affinity to the carbohydrate or saccharide which has been separated.

The conjugates formed by binding carbohydrates to the tri-functional moieties generally have the characteristics 1–3 indicated above. A preferred class of such tri-functional moieties also include (a) a primary amine (which can be used to react with and bind to the hydroxyl group of a saccharide); (b) one or more ionizable groups which form charged groups (which allow movement within a charged field); (c) a fluorescent moiety (which allows the bands of separated material to be visualized under U.V. light); and (d) a relatively small molecular weight, e.g., less than 500, preferably in the range of about 200 to about 300 (so that the size of the tri-functional moiety does not interfere substantially with the electrophoretic separation.

A preferred embodiment of the present invention may be carried out by preparing a modified form of a 1-amino-4-naphthalene sulfonic acid (ANSA). The modified ANSA is prepared by reacting the ANSA with a light-sensitive azido-group. The azido-group is of course kept out of contact with the light (capable of activating the group) prior to and during the reaction.

The 1-amino-4-naphthalene sulfonic acid (ANSA) used in connection with the present invention has the following structure:

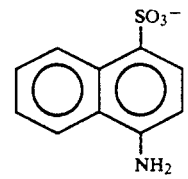

The —NH$_2$ amino group is indicated as being at the "1" position and the —SO$_3^-$ group is at the "4" position. The shared double bonds in each ring structures provides the fluorescent character to the ANSA when the ANSA is exposed to U.V. light.

The ANSA molecule is modified by the attachment of an azido-group which can be attached at any one of the positions either not already occupied by either the —SO$_3^-$ or the —NH$_2$ groups. The azido-group is the —N$_3$ group which may be connected directly to the ring structure or connected via a linking group. The azido-group will connect at the 5, 6, 7 or 8 position of the ANSA.

The modified ANSA molecule referred to above provides for the simplest form of the present invention in that the azido-group modified ANSA molecule provides all three functionalities on a single moiety, that is the modified ANSA molecule provides a charge, fluorescent capability and light-activatable attachment ability via the light-activatable azido group. However, as indicated above, it is possible to provide these three functionalities via three separate moieties.

When a mono-functional moiety is to be attached directly to the carbohydrate, it is possible to use a moiety which is only capable of fluorescing, such as naphthalene, fluorescein, aminonaphthalene or aminofluorescein. When a mono-functional moiety capable of only providing a charge is to attached directly to a carbohydrate, it is possible to use a moiety, such as a sulfonate or carbonate and/or combinations thereof.

The moieties capable of fluorescing and the moieties capable of providing a charge upon ionization can of course be combined together to provide a bi-functional moiety. Some examples of such bi-functional moieties include the following: 1-amino-4-(2-hydroxyethyl)piperazine;
2-amine-9-hydroxyfluorene;
2-amino-6-hydroxy-8-mercaptopurine;
4-amino-6-hydroxy-2-mercaptopyrimidine monohydrate;
2-amino-4-hydroxy-6-methylpyrimidine;
4-amino-3-hydroxy-1-naphthalenesulfonic acid;
4-amino-6-hydroxy-1-naphthalenesulfonic acid;
6-amino-4-hydroxy-2-naphthalenesulfonic acid monohydrate;
7-amino-4-hydroxy-2-naphthalenesulfonic acid monohydrate;
3-amino-5-hydroxypyrazole;
4-amino-6-hydroxypyrazolo[3,4-d]pyrimidine;
4-amino-1-naphthalenecarbonitrila;
3-amino-2,7-naphthalenedisulfonic acid, monosodium salt;
7-amino-1,3-naphthalenedisulfonic acid, monopotassium salt;
2-amino-1-naphthalenesulfonic acid;
4-amino-1-naphthalenesulfonic acid;
5-amino-2-naphthalenesulfonic acid;
8-amino-2-naphthalenesulfonic acid;
4-amino-1,8-naphthalic anhydride;
4-amino-1,8-naphthalimide;
3-amino-2-naphthoic acid;
4-amino-1,2-naphthoquinone hemihydrate;
6-aminonicotinamide;
5-((2-aminoethyl)amino)naphthalene-1-sulfonic acid, sodium salt; and
N-(2-aminoethyl)-4-amino-3,6-disulfo-1,8-naphthalene, dipotassium salt.

Any salts of the above-listed acids or acids of the above-listed salts can also be used.

In accordance with the more preferred embodiments of the invention all three functionalities of the moiety are provided on a single molecule. The trifunctional moieties capable of providing a charge, fluorescing and having a light-activatable group can be produced using any of the above-listed bi-functional moieties and attaching thereto a light-activatable azido group.

On preferred class of charge-generating moieties capable of fluorescing can be generally described by the following general structural formula:

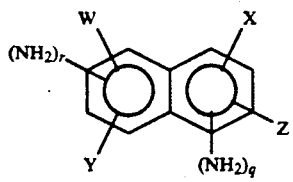

wherein each of W, X, Y and Z are independently hydrogen or an ionizable, charge-generating moiety such as $-SO_3^-$ or $-CO_2^-$, and q and r are independently 0 or 1 with the proviso that one of r or q is 1. Preferably only one of X is a charge generating moiety and it is preferably $-SO_3^-$. Further, alpha-amino naphthalenes are preferred over beta-amino naphthalenes. This preferred class of charge-generating moieties capable of fluorescing can be attached directly to a carbohydrate, such as a saccharide by itself and thereafter have the saccharide modified by attaching a light-activable azido-group. Preferably however, the above-described preferred class of charge-generating moieties capable of fluorescing is modified initially by the attachment of a light-activable azido-group which can be attached directly to any of the compounds encompassed by the above general structural formula or it can be attached via a linking group by methods well known to those skilled in the art. Such tri-functional moiety can then be attached to any carbohydrate, preferably saccharide, in order to provide a tri-functional conjugate which is believed to be a novel and unobvious compound of the present invention.

It will be recognized by those skilled in the art that different functional moieties may be preferred with respect to the separation of different types of saccharides and carbohydrates. For example, when separating relatively small saccharides such as mono-, di- and tri-saccharides it is not desirable to place a large charge on the saccharide in that the charge can overwhelm any other characteristics of the compound and thereby make it difficult to separate closely related smaller saccharides from each other. Regardless of the type of charge generating moiety, fluorescent moiety or light-activatable azido group which is attached to the carbohydrate, all three functionalities must be provided in order to obtain the objects and advantages of the present invention. When the three functionalities have been provided onto the carbohydrate the resulting conjugate is referred to herein as a "tri-functional conjugate."

The tri-functional conjugate is prepared by reacting the three functional groups with a mixture of saccharide compounds to be tested. As an example the azido-modified ANSA is bound to the saccharides in the mixture by connecting the saccharide to the ring structure of the ANSA at a position not previously occupied, thus forming saccharide/ANSA conjugates. Thus the tri-functional conjugates are formed in order to provide the saccharide molecules with: (1) a charge (e.g., obtained from the $-SO_3^-$ of the ANSA) which is necessary in order to carry out electrophoretic separation of the saccharide compounds; (2) a U.V. light fluorescent ability (e.g., obtained from the shared double bonds of ring structures of the napthalene); and (3) a light-activatable group (e.g., an azido group) which upon light activation binds to the substrate.

The tri-functional conjugates are then subjected to gel electrophoresis for a sufficient period of time to form separate groups of conjugates in the gel electrophoresis. The groups are generally present in the gel in specific bands which related in large part to the size, but also relate to the specific structure of the saccharides.

The separation techniques utilized in connection with the present invention have been found to work particularly well in connection with smaller saccharides. More specifically, the gel electrophoresis has been found to be particularly useful in separating mixtures of monosaccharides, disaccharides, and trisaccharides. Conventional procedures are generally not capable of providing sufficient resolution to separate away smaller saccharides into distinct bands. The addition of the ANSA group or other group of like charge, provides a sufficient amount of charge to allow for the separation of the smaller saccharides into distinct groups but does not apply too much charge so that the charge quality overwhelms any other quality of the saccharides and thus does not provide for resolution among different types of closely related saccharides. Further, the shared double bonds within the ring structures of the fluorescing moiety such as napthalene provide for the fluorescent capability. Accordingly, when different bands of saccharides are separated away from each other, it is possible to visually view these bands simply by the application of ultraviolet light. As will be described further below, the inclusion of the fluorescing group provides a number of important advantages to the present invention in that the fluorescing group makes the individual separated bands visible so that any given band can be removed and manipulated or tested in a given assay system.

The use of such a fluorescent tag provides a number of advantages over and above the use of other types of tags. For example, a fluorescent tag is substantially safer and less expensive than the use of a radiolabel. Further, the use of a fluorescent tag is substantially less cumbersome and more efficient than the use of antibody-linked enzyme tags. These advantages are obtained concurrently with the overall advantage of providing a tag which allows for greatly improved resolution especially as used in connection with smaller saccharide compounds.

It is possible to increase the ability to detect small amounts of carbohydrates or saccharides within bands by binding additional moieties which fluoresce but do not impart additional charge, e.g., napthalene alone. The inclusion of large additional charge would overwhelm the separation procedure to the extent that other characteristics of the saccharide would not be borne out when separating closely related smaller saccharides. However, by merely binding additional napthalene the fluorescent capability of the conjugate is increased without affecting the charge of the conjugate.

The separated bands of tri-functional conjugates within the gel are then transferred to the surface of a membrane. A number of different types of membrane surfaces can be utilized in connection with the invention. However, nylon is preferable. The transfer of the tri-functional conjugates such as the saccharide/ANSA/azido conjugates from the gel to the surface of the substrate is carried out by utilizing electro-blotting techniques. The electro-blotting is carried out for a sufficient period of time to allow substantial amounts of the conjugates within the gel to transfer to and bind to the surface of the substrate thus providing a permanent record of the separated bands of conjugates on the surface of the membrane.

The electro-blotting procedures which can be used in connection with the present invention are procedures which are generally known to those skilled in the art. In general, a gel having the separated conjugates thereon is placed in contact with a membrane surface. The membrane surface which is preferably a charged nylon surface is preferably first wetted with a buffer in which the electro-blotting procedure will be carried out. What is arbitrarily chosen as the cathode side of the gel (i.e., ultimately towards the negative electrode when positioned in the electro-blotting tank) is placed in contact with the surface of the nylon substrate after the substrate has been moistened with the electro-blotting buffer. Any air bubbles between the gel and the nylon membrane should be removed by gently pushing the nylon substrate against the gel using powder-free gloved fingers. A piece of nitrocellulose can be placed on the opposite side of the gel and all of the air bubbles should be removed between the gel and the nitrocellulose. Such a construct is then placed in the electro-blotting tank which contains a buffer solution and has an anode and a cathode therein. The power supply is then turned on and the power supply will draw the electrically charged tri-functional conjugate such as the saccharide/ANSA conjugates out of the gel and onto the charged surface of the nylon substrate. The transfer time is dependent somewhat on the thickness of the gel and the size of the conjugates being transferred to the nylon substrate. The transfer can be monitored by viewing the transfer under U.V. light to insure complete transfer of all of the materials to the nylon substrate surface. Overnight transfer is reliable and convenient.

One of the surprising discoveries of the present invention is that the specific bands of conjugates in the gel are even more clearly resolved and distinguishable from each other when the transfer is made to the nylon substrate surface. While not wishing to be bound to any particularly theory, it is believed that greater resolution is obtained on the nylon surface because of the diffusion of light in the gel when the conjugates are exposed to U.V. light. Regardless of the reason, it has been found that distinct, separate bands of conjugates are formed on the nylon substrate surface.

After the tri-functional conjugates have been secured to the membrane surface, the membrane is exposed to light of a sufficient frequency and for a sufficient time in order to activate the light-sensitive groups such as the azido-groups attached to the conjugates. Once the azido-groups are activated they provide an active group which tightly binds to, thus binding the whole conjugate to the nylon substrate surface. This binding is particularly important when the conjugates do not have a particularly large charge. For example, when the saccharide compounds being separated are substantially neutral with respect to charge, they will not bind very tightly to the nylon substrate surface. Accordingly, the light-activated azido-group provides for a secure binding of the conjugates to the nylon substrate surface so that the conjugates are not washed away during any subsequent washing steps.

It is important that the saccharide/ANSA/azido conjugates are securely bound to the nylon substrate surface in that these conjugates are to be used as receptors for labeled probes such as labeled proteins. When the labeled proteins are contacted to the substrate surface, they are allowed to stay in place for a sufficient time to allow for binding to occur between the probe and the conjugate, e.g., the tri-functional saccharide/ANSA/azido conjugate. However, in order to make the assay meaningful, the nylon substrate surface must be thoroughly washed in order to remove any probes which have not securely bound to the saccharides. During this washing procedure, the conjugates would themselves be washed away if they were not securely bound to the nylon substrate surface. If such conjugates were washed away, the sensitivity and accuracy of the assay would, of course, be substantially decreased.

Based on the above, it can be understood that the attachment of the light-sensitive azido-group is a particularly important aspect of the present invention. The azido-group can be attached to the saccharide or another functional moiety such as to any position on the rings of the napthalene of the ANSA which is not occupied. The attachment can be carried out by utilizing reaction schemes and reagents readily known to those skilled in the art. It is possible to attach the azido-group directly to a ring structure of a saccharide or napthalene or attach the azido-group via a linking group. Procedures for carrying out such attachments are described within the literature.

After the conjugates on the membrane surface have been secured to the surface, the specific saccharides within each of the visually detectable groups can then be tested for their affinity to other molecules. This testing is generally done by first forming conjugates of molecules to be tested by binding such molecules to a label. For example, protein molecules are bound to a radiolabel. The conjugates of radiolabeled proteins are then brought into contact with the saccharide conjugates on the surface of the membrane. If the proteins have an affinity to the saccharides on the membrane, they will bind to the saccharides, thus forming double conjugates, i.e., the saccharide conjugates bind to the protein/label conjugates.

After the protein/label conjugates have been allowed to remain in contact with the membrane surface for a sufficient period of time to allow for complete binding, the membranes are washed thoroughly in order to remove any unbound protein. After the unbound proteins are removed, the bound proteins, if any, are detected by utilizing the label attached to the proteins by procedures such as radiography.

The separation methodology of the present invention can be utilized in order to test a variety of different types of compounds for their affinity to the saccharides on the nylon substrate. For example, the invention can be utilized in order to test the affinity of certain lectins for their affinity to the saccharides. Particular types of antireceptor proteins known to be positioned on viruses and to be attachable to certain saccharides on cell surfaces can be tested. Further, the affinity of certain growth factor proteins can be tested. It is believed that the attachment of certain saccharides to growth factor proteins can effect the activity of the growth factor protein in vivo.

The molecules to be tested, such as the protein molecules to be tested for their affinity to saccharides, must, of course, be bound to a label which is later detectable. A variety of different types of labels known to those skilled in the art can, of course, be used. For example, it is possible to utilize radiolabels which are later detected by the use of autoradiography. It is also possible to attach the protein molecules to an antibody which itself is bound to an enzyme such as horseradish peroxidase which can be detected by the addition of reagents which cause a color change. Procedures for attaching the labels to the proteins or other molecules to be assayed are well known to those skilled in the art.

The following example is provided to as to give those of ordinary skill in the art a complete disclosure and description of how to carry out the separation and assaying steps of the invention and are not intended to limit the scope of what the inventors regard as their invention. Efforts have been made to insure accuracy with respect to numbers used (e.g., amounts, temperature), but some experimental errors and deviations should be accounted for. Unless indicated otherwise, parts or parts by weight, temperature is in degrees centigrade and pressure is at or near atmospheric.

EXAMPLE 1

A modified form of 1-amino-4-naphthalene sulfonic acid (ANSA) is formed by the addition of an azido-group. An appropriate azido-group is chosen and added to the ANSA at the 5, 6, 7 or 8 position of the naphthalene ring system. The azido-group is light-sensitive and therefore, should be kept out of contact with light of a frequency capable of activating the group. After the modified ANSA is formed, the modified ANSA has the ability to react with a reducing sugar via the primary amine of the ANSA at the 4 position of the ANSA and the negative charge is present at the 1 position of the ANSA thus providing for the charge necessary in electrophoretic separation techniques. Charged oligosaccharides are formed by reacting a mixture of oligosaccharides with the modified ANSA. The reaction is carried out in 10 to 100 mM sodium acetate buffer (pH 5.0). The oligosaccharides are present in an amount of 0.01-1 umol/ml and are reacted with the modified ANSA and sodium cyanoborohydride in a ten fold molar excess with respect to the reducing end sugar of the oligosaccharide. The derivatized oligosaccharides are then subjected to electrophoretic resolution in 40% acrylamide/5% bis gels, with a Tris/glycine buffer system (25 mM Tris, 195 mM glycine, pH 8.3). The electrophoretic gel is to be run at 300 volts for approximately 90 minutes. The gels are to be immediately electro-blotted using a Biorad apparatus onto a Zetaprobe membrane (of the type commercially sold by Biorad). The electro-blotting is carried out utilizing standard techniques and 100 volts for one hour with the same Tris/glycine buffer system. After completing the electro-blotting, the Zetaprobe membranes are removed and air dried. The membranes are then exposed to light which activates the azido-groups thus providing for an active group which tightly binds to the membrane surface. Accordingly, the dried membranes have the highly resolved bands of saccharide/modified ANSA conjugates bound tightly thereon.

For purposes of a comparison, it is preferable to cut the Zetaprobe membranes into a plurality of lanes. This cutting provides multiple copies of the highly resolved saccharide/ANSA conjugate groups. These highly resolved groups are clearly visible under ultraviolet light due to the presence of the shared double bonds within the ring structures of the ANSA.

After the azido-groups are activated and the conjugates are bound by the light activation procedure, they may be probed with proteins (radioiodinated bFGF) overnight at 4° C., in PBS plus 2% PVP40. After allowing any binding to take place, the membrane are washed with the same buffer three times, and then dried. Bound protein can be detected by autoradiography. The ANSA fluorescent label on the oligosaccharide will allow for the direct visualization of the blot and comparison of it with the autorad, i.e., the membrane having the radiolabeled proteins bound thereto.

The above procedure is particularly useful with respect to the resolution of different saccharides which are relatively small in size, e.g., mono-, di- and trisaccharides. This is particularly true when the saccharides in the mixture of saccharides being tested are relatively neutral in charge. The procedure allows for the assaying of large numbers of saccharides by a relatively simple and inexpensive procedure. Further, once large numbers of saccharides are resolved via the present procedure, it is possible to readily test the affinity of these saccharides to large numbers of proteins. Accordingly, the present invention provides not only a means for separating and resolving large numbers of saccharides of different types from one another, but provides a further means for assaying for the affinity of specific resolved saccharides to specific proteins and/or other compounds which may have an affinity to such saccharides.

The instant invention is shown and described herein in what is considered to be the most practical, and preferred embodiments. It is recognized, however, that departures may be made therefrom which are in the scope of the invention and that obvious modifications will occur to one skilled in the art upon reading this disclosure.

We claim:

1. A method of separating mixtures of saccharides into distinct detectable groups, comprising the steps of:
   reacting the mixture of saccharides with moieties (a) capable of providing a charge, (b) capable of fluorescing under ultra violet light; and (c) having a light-activatable azido group thereon to provide tri-functional conjugates;
   subjecting the tri-functional conjugates to gel electrophoresis for a sufficient period of time to form separate groups of conjugates in the electrophoresis gel;
   electro-blotting the separate groups of conjugates from the gel onto the surface of a membrane; and
   subjecting the conjugates on the membrane to light for a sufficient time and of a light frequency which activates the light-sensitive azido-group.

2. The method as claimed in claim 1, wherein the moieties (a) capable of providing a charge, (b) capable of fluorescing under ultraviolet light, and (c) having a light-activatable azido group thereon are the same moieties which are charge generating moieties capable of fluorescing and having an azido group thereon.

3. The method as claimed in claim 2, wherein the tri-function moiety is in the form of an azido-group bound to the naphthalene ring system of 1-amino-4-napthalene sulfonic acid at the 5, 6, 7 or 8 position.

4. A method as claimed in claim 3, wherein the azido-group is connected directly to the naphthalene ring system.

5. A method as claimed in claim 3, wherein the azido-group is connected to the naphthalene ring system via a linking group.

6. The method as claimed in claim 1, wherein the moieties (a) capable of providing a charge, (b) capable of fluorescing under ultraviolet light, and (c) having an azido group thereon are each separate moieties which are individually attached to the saccharides.

7. The method as claimed in claim 1, further comprising:
   contacting the separate groups of conjugates on the membrane with labeled probes to determine the affinity of the probes to bind to a group of conjugates.

8. The method as claimed in claim 7, further comprising:
   washing away any labeled probes not bound to a group of conjugates and detecting bound probes by their label.

9. The method as claimed in claim 7, wherein the labeled probe is a labeled protein probe.

10. The method as claimed in claim 9, wherein the label is a radiolabel.

11. The method as claimed in claim 9, wherein the labeled protein probe is a labeled antireceptor protein of a virus.

12. The method as claimed in claim 9, wherein the electrophoresis gel is comprised of about 40% acrylamide, about 5% bis gels, in a Tris-glycine buffer system.

13. The method as claimed in claim 12, wherein the Tris-glycine buffer system includes approximately 25 mM Tris, approximately 195 mM glycine and has a pH of about 8.3.

14. The method as claimed in claim 1, wherein the saccharide mixture includes saccharides selected from the group consisting of mono-, di- and trisaccharides.

15. The method as claimed in claim 14, wherein the saccharide is a monosaccharide.

16. The method as claimed in claim 14, wherein the saccharide is an disaccharide.

17. The method as claimed in claim 14, wherein the saccharide is a trisaccharide.

18. A tri-functional carbohydrate conjugate in the form of a carbohydrate covalently bound to a moiety (a) capable of providing a charge upon ionization; (b) capable of fluorescing under ultra violet light; and (c) which is light-activatable, the light-activatable group being in the form of an azido-group.

19. A method of resolving a mixture of saccharides into distinct groups of closely related or identical saccharides, comprising the steps of:
   reacting the mixture with moieties (a) capable of providing a charge upon ionization; (b) capable of fluorescing when exposed to ultraviolet light; and (c) having a light-activatable azido group thereon to provide tri-functional conjugates;
   subjecting the tri-functional conjugates to gel electrophoresis for a sufficient period of time to form separate groups of conjugates in the electrophoresis gel;
   transferring the separate groups of conjugates in the electrophoresis gel to a membrane surface; and
   subjecting the conjugates on the membrane surface to light for a sufficient time and of a light frequency which activates the light-sensitive azido-group and creates a binding between the azido-group and the surface.

20. The method as claimed in claim 19, wherein the moieties (a) capable of providing a charge; and (b) capable of fluorescing under ultraviolet light are the same moieties and wherein the moiety having a light-activatable azido group thereon is a separate moiety attached to the saccharides.

21. The method as claimed in claim 20, wherein the moieties (a) capable of providing a charge; and (b) capable of fluorescing under ultraviolet light are napthalene sulfonic acids, or derivatives thereof.

22. The method as claimed in claim 19, wherein the membrane is a charged nylon membrane.

23. The method as claimed in claim 19, wherein the saccharide mixture comprises saccharides selected from the group consisting of monosaccharides, disaccharides and trisaccharides.

24. The method as claimed in claim 23, further comprising:
   contacting the separate groups of conjugates on the nylon membrane with labeled probes to determine the affinity of the probes to bind to the saccharides in the separate groups.

25. The method as claimed in claim 24, further comprising:
   washing a way any labeled probes not bound to a saccharide and detecting bound probes by their label.

26. A method for assaying for the affinity of a protein for a saccharide in a mixture of saccharides, comprising the steps of:

reacting the mixture of saccharides with moieties (a) capable of providing a charge upon ionization; (b) capable of fluorescing under ultraviolet light; and (c) having a light-activatable azido group thereon in order to provide tri-functional conjugates;

subjecting the tri-functional conjugates to gel electrophoresis for a sufficient period of time to form separate groups of conjugates in the electrophoresis gel;

electro-blotting the separate groups of conjugates from the gel onto the surface of a membrane;

subjecting the conjugates on the membrane to light for a sufficient time and of a light frequency which activates the light-sensitive azido-group which binds to the surface of the membrane; and contacting the membrane having the conjugates thereon with labeled proteins to determine the affinity of the proteins to bind to saccharides on the membrane.

27. The method as claimed in claim 26, further comprising:

washing away any labeled proteins not bound to saccharides on the membrane surface and detecting bound proteins.

* * * * *